United States Patent
Wang et al.

(10) Patent No.: US 8,279,435 B2
(45) Date of Patent: Oct. 2, 2012

(54) NANOSTRUCTURED METAL-POLYANILINE COMPOSITES AND APPLICATIONS THEREOF

(75) Inventors: Hsing-Lin Wang, Los Alamos, NM (US); Wenguang Li, North Andover, MA (US); James A. Bailey, Los Alamos, NM (US); Yuan Gao, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 148 days.

(21) Appl. No.: 12/619,328

(22) Filed: Nov. 16, 2009

(65) Prior Publication Data

US 2010/0060894 A1    Mar. 11, 2010

Related U.S. Application Data

(62) Division of application No. 11/653,004, filed on Jan. 11, 2007, now Pat. No. 7,786,037.

(51) Int. Cl.
*G01J 3/44* (2006.01)
*C07C 5/03* (2006.01)
*C07C 51/36* (2006.01)
*C07F 7/10* (2006.01)
*B01J 35/00* (2006.01)

(52) U.S. Cl. ............ 356/301; 502/4; 585/268; 556/413; 562/494

(58) Field of Classification Search .................. None
See application file for complete search history.

(56) References Cited

OTHER PUBLICATIONS

Drelinkiewicz et al. Synthetic Metals, 102 (1999) 1307-1308.*

* cited by examiner

*Primary Examiner* — Melvin C Mayes
*Assistant Examiner* — Yun Qian
(74) *Attorney, Agent, or Firm* — Juliet A. Jones; Bruce H. Cottrell; Samuel L. Borkowsky

(57) ABSTRACT

Metal-polyaniline (PANI) composites are provided together with a process of preparing such composites by an electrodeless process. The metal of the composite can have nanoscale structural features and the composites can be used in applications such as catalysis for hydrogenation reactions and for analytical detection methods employing SERS.

10 Claims, 9 Drawing Sheets

NANOSTRUCTURED METAL-POLYANILINE COMPOSITES AND APPLICATIONS THEREOF

REFERENCE TO PRIOR APPLICATION

This application is a divisional application of U.S. patent application Ser. No. 11/653,004, filed Jan. 11, 2007, now U.S. Pat. No. 7,786,037.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates to metal-polyaniline composites, e.g., nanostructured metal-polyaniline composites, to the preparation of such metal-polyaniline composites, e.g., metal-polyaniline composites, e.g., such nanostructured metal-polyaniline composites, to the use of such metal-polyaniline composites, e.g., metal-polyaniline composites, e.g., such nanostructured metal-polyaniline composites in catalysis applications and to the use of such metal-polyaniline composites, e.g., metal-polyaniline composites, e.g., such nanostructured metal-polyaniline composites in applications employing surface enhanced Raman scattering (SERS).

BACKGROUND OF THE INVENTION

In the past few decades, there has been an increasing interest in using conducting polymers to fabricate electronic or optical devices such as light-emitting diodes and molecular electronics. Polyaniline (PANI) has been one of the most commonly used conducting polymers due to its facile synthesis, lower cost and environmental stability and has been carefully examined for use in electromagnetic shielding and anti-corrosion coatings.

PANI possesses secondary and tertiary amines in the backbone structure that can bind metal ions. The metal ions can be released from the PANI by immersion of the PANI into a low pH solution. The ability of PANI to bind metal ions and to subsequently release them has made PANI an attractive material for environmental remediation. In cases where metal ions have a reduction potential higher than that of the PANI, the bound metal ions can be reduced to form zero-valent metals. Thus, it has been recognized that PANI can be used for the electrodeless precipitation of metals from a metal ion solution.

Reduction and precipitation of gold from acid-solutions using conducting polymers has been shown for the recovery of gold from solutions (Kang et al., Journal of Chemical Technology and Biotechnology, 1994, 59, 31-36). Metallization of printed circuit boards using PANI has also been shown (Huang et al., Molecular Crystals and Liquid Crystals, 1990, 189, 227-235).

Despite the prior work on deposition of metals using polyaniline, the nature of the metal structure, e.g., nanostructure, on the conducting polymer surface has not been controllable. The metals deposited in prior work are featureless, particularly at the nanoscale level, simply serving the purpose of being electrical conductors.

SUMMARY OF THE INVENTION

The present invention provides a metal-polyaniline composite including a layer of polyaniline having at least one surface, and, metal deposited upon at least one surface of said layer of polyaniline, said metal characterized by its salt form having a reduction potential greater than that of the polyaniline.

In one aspect, the present invention provides a process of preparing metal-polyaniline composites by contacting a metal ion solution with a PANI porous asymmetric membrane for a period of time sufficient to form said metal-PANI composite, said metal characterized as its salt form having a reduction potential greater than that of the polyaniline.

In one aspect, the present invention further provides a process of catalyzing a hydrogenation reaction to obtain a hydrogenated product including reacting an unsaturated organic compound with hydrogen for sufficient time in the presense of a metal-PANI composite, the PANI from the group of a PANI porous asymmetric membrane and a thermally cured PANI dense film and the metal from the group of platinum and palladium, and, recovering a hydrogenated product. The metal-PANI composites provide an easily recoverable and reusable catalytic media for hydrogenation reactions.

In another aspect of the present invention, the metal-polyaniline composites are used in a process of detecting a target material using surface enhanced Raman scattering (SERS).

DETAILED DESCRIPTION

Figure 1:
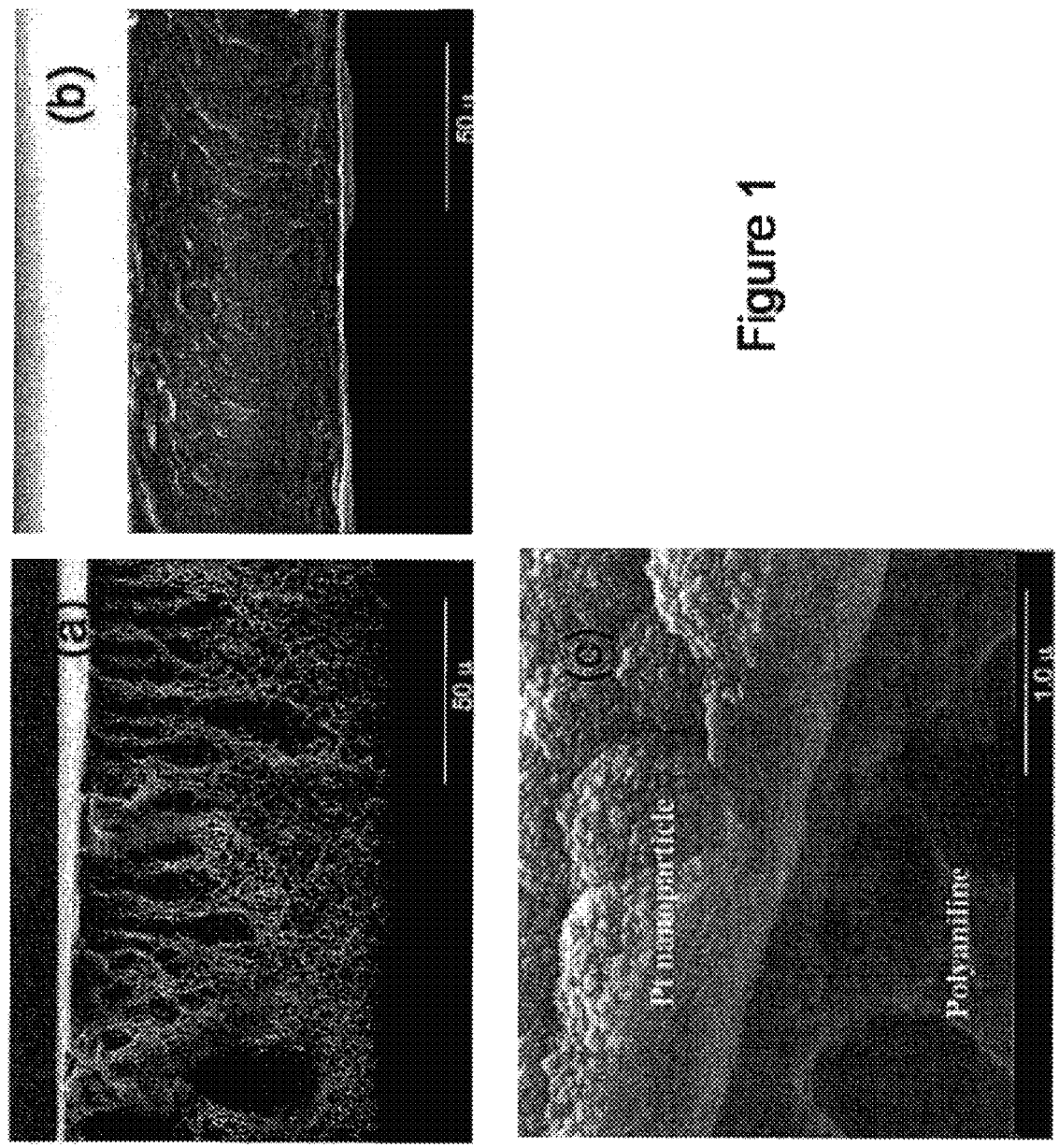
FIG. 1 show: scanning electron microscopy (SEM) micrographs showing a cross-section of: (a) a porous asymmetric PANI membrane; (b) a thermally cured dense PANI film; and, (c) a porous asymmetric PANI membrane having a layer of platinum nanoparticles deposited thereon.

The present invention is concerned with the metal-polyaniline composites, e.g., nanostructured metal-polyaniline composites and to the preparation of such metal-polyaniline composites, e.g., such nanostructured metal-polyaniline composites. The present invention is also concerned with the use of such metal-polyaniline composites, e.g., such nanostructured metal-polyaniline composites in catalysis applications and to the use of such metal-polyaniline composites, e.g., such nanostructured metal-polyaniline composites in applications employing surface enhanced Raman scattering (SERS).

The term "asymmetric membrane" refers to a thin skin of polymer is grown on a porous structural polymer support. The term "SERS" refers to surface enhanced Raman spectroscopy.

In the present invention, metal-polyaniline composites can be prepared by electrodeless deposition using a conductive polymer such as PANI. The reduction potential of PANI at its emeraldine base form versus a standard reference hydrogen electrode is from about 0.70 V to 0.75 V whereas PANI at its leucoemeraldine base form versus a standard reference hydrogen electrode is from about 0.30 V to 0.40 V. Where the particular metal ions have a reduction potential greater than that of the PANI, simple immersion of a suitable PANI film or membrane into an aqueous solution of the particular metal ions can result in the deposition of metal upon the PANI and form the metal-PANI composite. For silver nitrate (reduction potential of 0.8 V), gold chloride (reduction potential of 1.5 V), and platinum chloride (reduction potential of 0.755 V), a metal coating including metal nanoparticles can form upon a PANI porous asymmetric membrane or thermally cured PANI dense film dipped into the aqueous metal salt solution. Metals useful in the composite structures of the present invention can generally include metals such as gold, silver, platinum, palladium and the like.

Polyaniline is used in the composite of the present invention because it is cheap, easy to synthesize and environmentally stable. It has several oxidation states (leucoemeraldine base, emeraldine base, and pernigranilin base), and its oxidation states can be controlled easily through chemical and electrochemical methods.

Other conducting polymers may also be useful in place of polyaniline in the present invention and may generally include polypyrrole, polythiophene, poly(phenylene vinylene) or other widely known other conducting polymer materials to yield similar results.

Polyaniline is the name given to the polymer having the structure, in a completely reduced leucoemeraldine oxidation state, of the general formula:

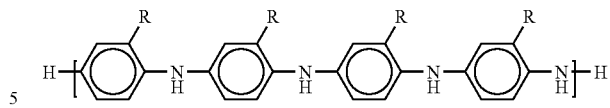

where n is greater than about 5 and where R is a hydrogen atom. Alternatively, R may be a substituent, such as, for example, an organic group, including, for example, $CH_3$, $C_2H_5$, $OCH_3$, $N(CH_3)_2$, an inorganic group, including, for example, F, Cl, Br, I, or a metal chelate group. For the polyanilines described herein, the appropriate choice of an R group permits a greater range of solubility in a greater number of different types of solvents, which results in increased versatility for processing the polymers and a greater range of chemical properties.

Typically, PANI can be cast from solution, hot-pressed into a fully dense film or otherwise processed into a hollow fiber or asymmetric membrane. Asymmetric PANI membranes can be made by using a non-solvent during the phase inversion process, e.g., by adding methanol or water to polyaniline in N-methyl pyrrolidone during film formation. One example of the preparation of asymmetric PANI membranes is described by Wang et al. in U.S. Pat. No. 6,797,325, such description incorporated herein by reference.

The use of PANI porous asymmetric membranes for the chemical deposition of metal layers, e.g., nanostructured metal layers has an advantage of lower density as compared to thermally cured dense PANI films. The structure of such porous PANI asymmetric membranes have been well characterized previously (see Wang et al., Chemistry of Materials; vol. 14, no. 6, pp 2546-2552 (2002)). FIG. 1 shows the difference between a PANI porous asymmetric membrane and a thermally cured PANI dense film. The lower density allows diffusion of metal ions between PANI chains, which may aid the nucleation process. Furthermore, the PANI membranes prepared by the phase inversion process does not involve heat treatment for a prolonged time period. The phase inversion process allows PANI to maintain its original redox states and is believed to minimize crosslinking between PANI chains. While the reasons are not wholly understood, there are clear differences in metal morphologies grown from thermally cured PANI dense films and those grown from PANI porous asymmetric membranes. Deposition of metals on top of PANI surfaces can be achieved simply by immersing either prefabricated PANI membranes or prefabricated thermally cured dense PANI films into an aqueous metal ion solution with metal ion concentrations ranging from about 0.01 Molar (M) to about 1.0 M. The time period necessary for the metal growth ranges from about several seconds to about several hours depending upon the experimental conditions such as temperature and metal ion concentration. The membranes are typically left in solution until metal deposition can be observed visually on the target surface whether the porous membranes or the dense films.

Figure 2:
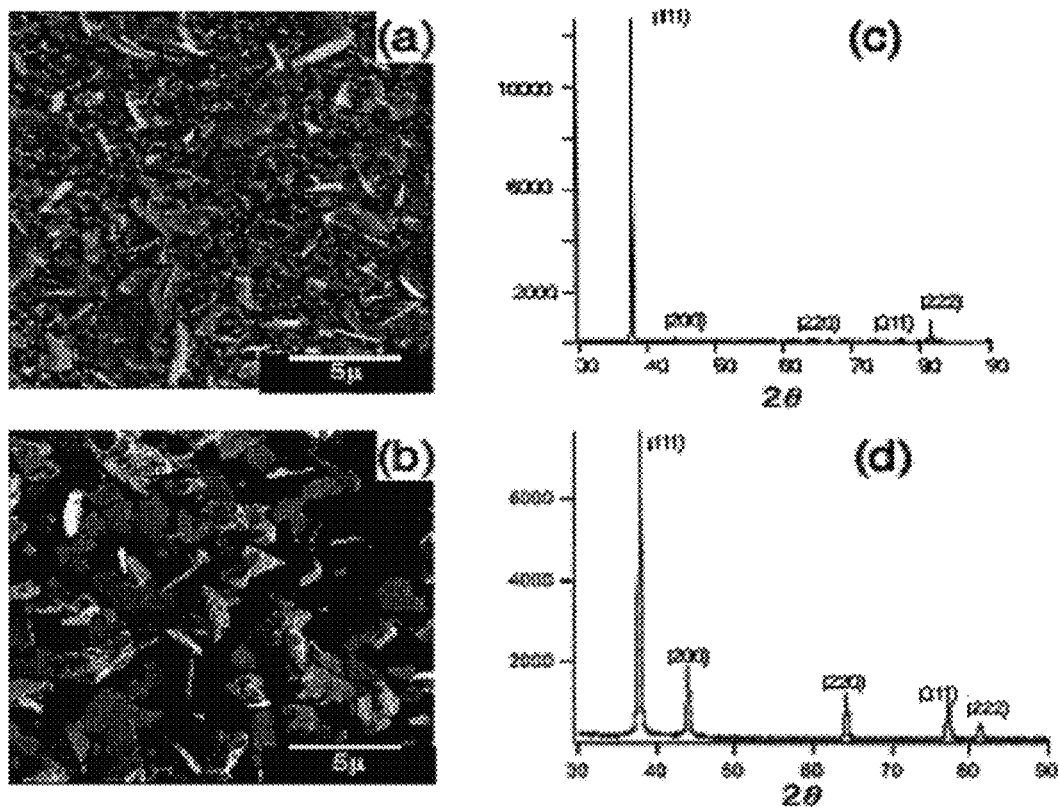
FIG. 2 shows SEM micrographs of: (a) silver deposited upon an undoped PANI asymmetric membrane; (b) silver deposited upon an HCl doped PANI asymmetric membrane; and X-ray diffraction patterns of (c) the silver coated undoped PANI asymmetric membrane shown in (a); and, (d) the silver coated HCl doped PANI asymmetric membrane shown in (b).

FIG. 2(a) and FIG. 2(b) show the SEM images of the evenly distributed silver metal grown on top of the undoped and doped PANI porous asymmetric membranes. The morphological differences between the doped and undoped examples are obvious. FIG. 2(a) shows very thin silver sheets spread evenly on top of the PANI porous asymmetric membrane surface. Higher surface coverage of silver sheets on the undoped PANI membrane suggests favorable interaction between silver and the undoped PANI. Furthermore, most of the silver sheets have an estimated thickness of less than a few nanometers, appearing as transparent during high-voltage SEM imaging. In contrast to the silver sheets on the undoped PANI porous asymmetric membrane, silver on the HCl doped PANI porous asymmetric membrane showed a random morphology. Silver sheets with thicknesses of 20 nanometers (nm) and large globular silver particulates are approximately equally distributed on the membrane surface. The SEM image also revealed less surface coverage of silver on the doped PANI porous asymmetric membranes. The presence of silver was further confirmed by the XRD spectra clearly identifying the five silver peaks, as seen in FIG. 2(c) and FIG. 2(d).

In addition to the difference in morphology, XRD spectra also indicated anisotropy of silver on the undoped PANI porous asymmetric membrane surface (see FIG. 2(c)). XRD scan of these silver sheets on the undoped PANI porous asymmetric membrane surface clearly showed (111) and (222) preferential orientation since (200), (220), and (311) peaks are barely above the background signal. These results suggest that silver sheets on the undoped PANI porous asymmetric membrane surface preferentially grow along the [111] direction.

Thus, the present invention shows that the deposition of silver metal with different structures and morphologies can be achieved by simply varying the redox states of the PANI membrane.

Figure 3:
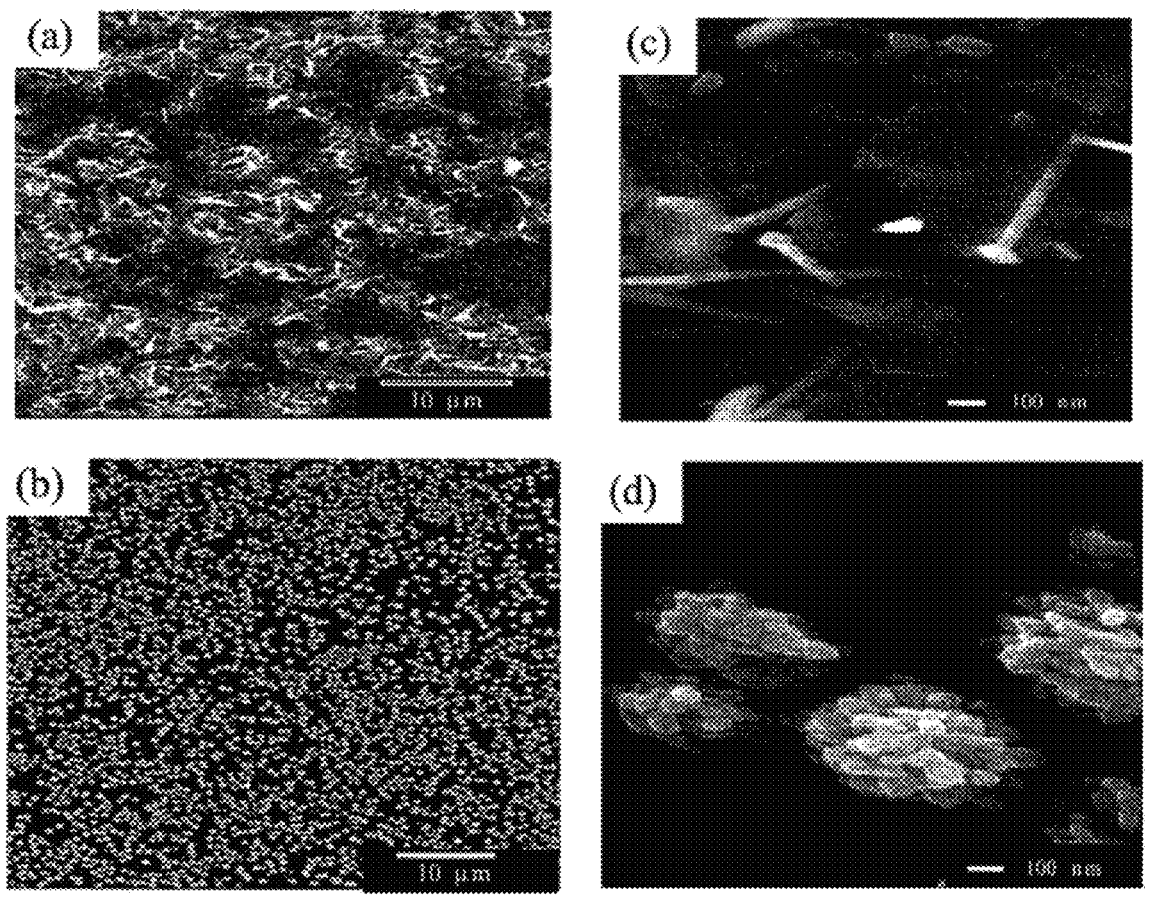
FIG. 3 shows SEM micrographs of: (a) gold deposited upon an undoped PANI asymmetric membrane; (b) gold deposited upon an HCl doped PANI asymmetric membrane; (c) a magnified view of the gold deposited upon an undoped PANI asymmetric membrane; and, (d) a magnified view of the gold deposited upon an HCl doped PANI asymmetric membrane.

Following similar procedures, chemical deposition of gold metal on the PANI porous asymmetric membranes, both doped and undoped. On the undoped PANI porous asymmetric membranes, the results showed mostly gold sheets together with some scattered nanoparticles (about 100 nm). High surface coverage indicated favorable interaction between gold sheets and undoped PANI porous asymmetric membranes, resembling the silver deposition on the same surfaces. Deposition of gold on the doped PANI porous asymmetric membranes showed a uniform morphology with evenly dispersed gold particulates on the membrane surfaces. SEM images (FIG. 3(d)) showed submicrometer-size gold particulates that are on closer examination actually conglomerates of smaller gold nanoparticles with rice-grain morphology. The total number of the smaller rice-grain gold nanoparticles determined the size of the conglomerates.

Figure 4:
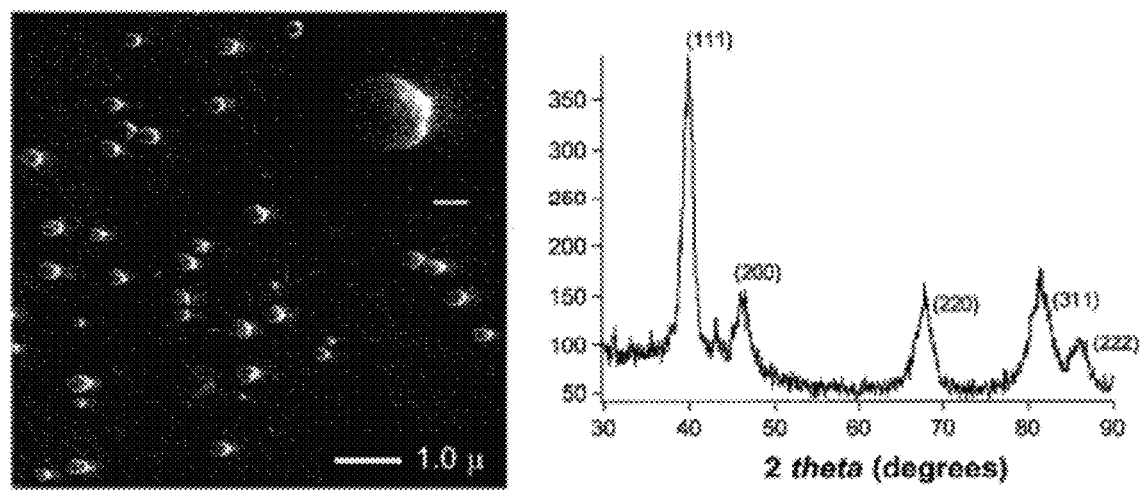
FIG. 4 shows: (a) a SEM micrograph of platinum nanoparticles deposited upon an undoped PANI asymmetric membrane; and; (b) an X-ray diffraction pattern of the platinum nanoparticle coated undoped PANI asymmetric membrane shown in (a). The inset shows that the larger platinum cluster consists of an ensemble of smaller nanoparticles (scale bar 100 nm).

Platinum ions could also be reduced by PANI to form platinum metal due to its higher reduction potential compared to that of the PANI. Deposition of platinum metal on the undoped PANI porous asymmetric membrane surfaces appeared as a layer of platinum nanoparticles together with some large platinum clusters having an estimated size distribution of from about 100 nm to about 300 nm (see FIG. 4). Although the exact dimension and size distribution of these nanoparticles was not determined, high resolution SEM indicated that most of these nanoparticles are less than about 10 nm in size. Close examination of these large clusters (inset of FIG. 4) indicated that they were conglomerates of smaller platinum nanoparticles. This was further supported by the XRD spectrum of a platinum coated PANI porous asymmetric membrane. The XRD spectrum not only showed diffraction peaks from different crystallographic orientations, it also showed a very broad full width at half-maximum from each diffraction peak. The particle size calculated based on the extra breadth or broadening due to the particle-size effect alone from XRD lines was about 5 nm, which is consistent with the high-resolution SEM results. While it might be that the XRD peaks of the larger platinum clusters might have been overwhelmed by the much smaller nanoparticles, the larger particles actually often dominate the overall XRD spectrum as they show a much sharper peak with higher intensity. These broad XRD peaks suggest that the larger platinum particulate is indeed composed of many platinum nanoparticles. These results thus show that simply immersing PANI porous asymmetric membranes into a $PtCl_4^{2-}$ aqueous solution can form platinum nanoparticles. While not wishing to be bound by the present explanation, it is believed that the very small difference in reduction potential (only about 0.05 Volts (V)) between PANI and $PtCl_4^{2-}$ led to a slower nucleation rate thus leading to the formation of smaller nanoparticles.

Figure 5:
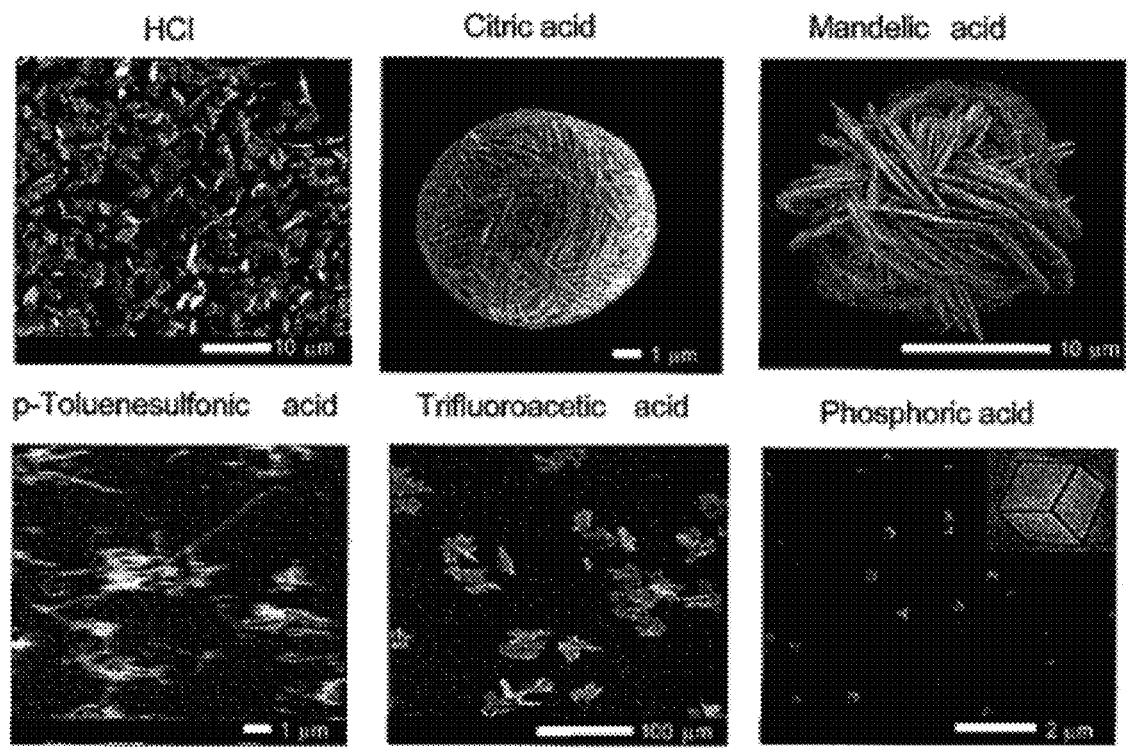
FIG. 5 shows SEM micrographs of silver deposited on PANI asymmetric membrane surfaces doped with (a) hydrochloric acid; (b) citric acid; (c) mandelic acid; (d) p-toluenesulfonic acid; (e) trifluoroacetic acid; and, (f) phosphoric acid.

The role of dopants of the PANI was examined to determine any effect upon structure and/or morphology. Six different pieces of the PANI porous asymmetric membrane were doped with one of the following: hydrochloric acid (HCl), phosphoric acid ($H_3PO_4$), trifluoroacetic acid ($CF_3COOH$), citric acid (2-hydroxypropane-1,2,3-tricarboxylic acid), mandelic acid (2-phenyl-2-hydroxyacetic acid) or para-toluenesulfonic acid (p-$CH_3C_6H_5SO_3H$). These doped membranes were then immersed into a 0.01 silver nitrate ($AgNO_3$) solution. The resulting deposited silver metal exhibited completely different morphologies as seen in FIG. 5. Silver grown on an HCl-doped PANI porous asymmetric membrane had a random morphology, while silver deposited on a citric acid-doped PANI porous asymmetric membrane had a yarn-ball like morphology. It should be noted that a close examination of the hemispheric yarn ball showed that rather than being composed of silver nanowire, it consisted of close-packed silver sheets with a thickness of about 25 nm, similar to that of silver grown on mandelic acid-doped PANI membrane surfaces. Silver nanowires of 20 nm in diameter were observed on the p-toluenesulfonic acid-doped PAHI membrane surfaces. Silver grown on trifluoroacetic acid-doped PANI membrane surfaces had a leaf-like morphology. Silver grown on the phosphoric acid-doped PANI membrane surfaces showed a cube-like morphology with 200 nm dimensions on the sides. In each of the six samples the deposited silver metal was characterized using XRD and energy dispersive X-ray analysis (EDAX). The five peaks in XRD spectra assigned as (111), (200), (220), (311) and (222) were positively identified to support the deposition of nanostructured silver metal on the PANI membrane surface as opposed to a silver salt. These results show that the size and morphology of deposited metal upon PANI membrane surfaces can be varied by the choice of dopant.

Figure 6:
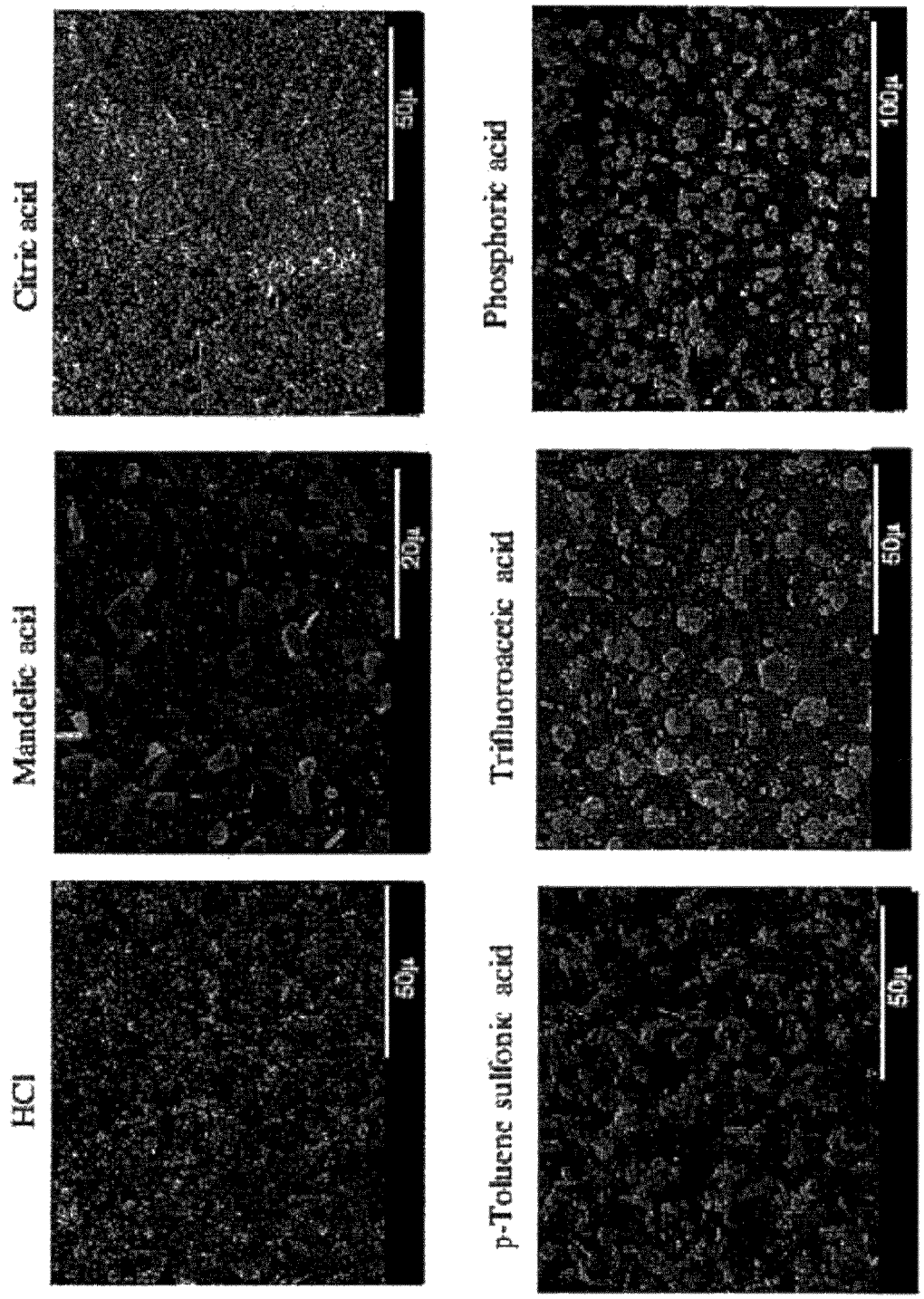
FIG. 6 shows SEM micrographs of silver deposited on thermally cured PANI dense film surfaces doped with (a) hydrochloric acid; (b) citric acid; (c) mandelic acid; (d) p-toluenesulfonic acid; (e) trifluoroacetic acid; and, (f) phosphoric acid.

Metal deposition on the PANI membrane surfaces through reduction requires electron transfer from the PANI to the metal ions. As the metal ions approach the PANI membrane surface, they can be reduced by the PANI and form nuclei. In a conventional homogeneous system, where metal ions and a reducing agent are both dispersed in solution, the metal nuclei can serve as catalytic sites for subsequent surface growth allowing the formation of larger metal structures. The present invention involves a heterogeneous system. In such a heterogeneous system, metal ions are reduced on the PANI membrane surface and the growth mechanism can be expected to differ from a homogeneous system. While not wishing to be bound by the present explanation, the size of the metal nuclei is likely to be dominated by the difference in reduction potential between metal ions and the PANI and by the surface properties of the PANI membrane substrate. The morphological difference corresponding to the various dopants may be influenced by the surface energy of the PANI membrane. The surface energy of the PANI membrane, manifested by the water contact angles, can be tuned by the nature of the dopants and the redox states of the PANI membrane Metals were also grown on thermally cured PANI dense films. The growth of metals on the thermally cured PANI dense films exhibited less variation in their morphologies as is shown in FIG. 6. In general, the silver growth on top of a series of thermally cured PANI dense films doped with the same dopants as before exhibited large structures, greater than a few microns, with random morphology. The exception was the mandelic acid-doped thermally cured PANI dense film, which yielded large silver platelets having a thickness of about 20 microns (μm). Also interesting was the observation that all of the acid doped thermally cured PANI dense films exhibited growth of nanocubes with dimensions ranging from about 60 nm to 200 nm, similar to the silver nanocubes grown on top of the phosphoric acid doped PANI porous asymmetric membranes. Most of the nanocubes were very small and a large number of them on the thermally cured PANI dense film surfaces made the films appear cloudy.

Figure 7:
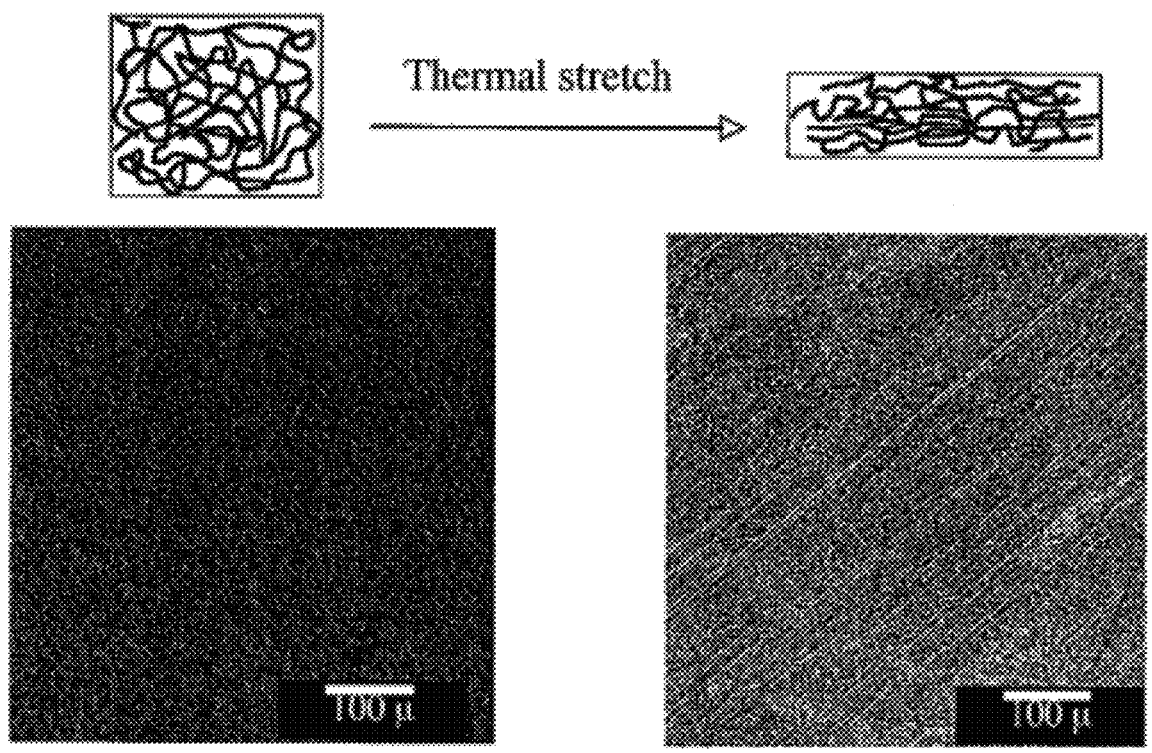
FIG. 7 shows: SEM micrographs of homogenously dispersed silver particles deposited on: (a) an unstretched thermally cured PANI dense film surface; and (b) a stretched thermally cured PANI dense film surface. It is seen that the silver particles deposit preferentially along the stretched direction with the arrow showing the stretched direction.

Control of metal growth could also be achieved by using a stretched PANI film (a thermally cured PANI dense film). The stretching of the PANI dense films can generally be from about 100 percent to 500 percent of the original size, more preferably from about 100 percent to about 400 percent of the original size. The contrast between silver deposited on the stretched and unstitched PANI dense film is shown in FIG. 7. A preferential deposition of the silver on the PANI dense film surface coincided with the stretched direction. In contrast, the unstitched PANI dense films exhibited homogeneous silver deposition throughout the PANI dense film surface. Such a preferential silver deposition is speculated to result from the lower reduction potential of the stretched oriented PANI dense film. The stretched (extended) PNI chain conformation leads to formation of crystalline regions having lower reduction potential and higher conductivity that the unstretched film portions.

The metal-PANI composites of the present invention can provide good catalytic activity to various organic reactions especially toward hydrogenation reactions. As the metal, e.g., metal nanoparticles, are stably adfixed to the PANI membrane, it can be easily recycled and reused whereas typical commercially available metal catalysts, e.g., Pd on C, can only be used once.

In one embodiment, metal-PANI composites of the present invention wherein the metal is platinum or palladium can be used in the selective hydrogenation of alkenes and alkynes.

Surface roughness has been considered an important factor that governs SERS. It has been previously observed that molecules near roughened silver surfaces show enhanced Raman scattering of as much as two orders of magnitude or more. The ability to detect and identify trace amounts of chemicals has become increasingly important. SERS has proven to be one of the most sensitive methods for performing chemical analysis by the detection of a single molecule. SERS offers the advantage of trace detection by increasing the scattering light intensity by as much as ten billion times especially with nanostructured metals such as silver and gold.

The SERS affect leads to a major increase of the Raman scattering cross-section for molecules absorbed onto suitably rough surfaces. Thus, use of the composites of the present invention in SERS applications has a large potential in analytical chemistry and for biological applications. (see U.S. Pat. No. 7,133,129) The structures of the present invention result in an enhancement of the localized electric field, which subsequently increases the SERS from the metal particles in the composite structures.

Figure 9:
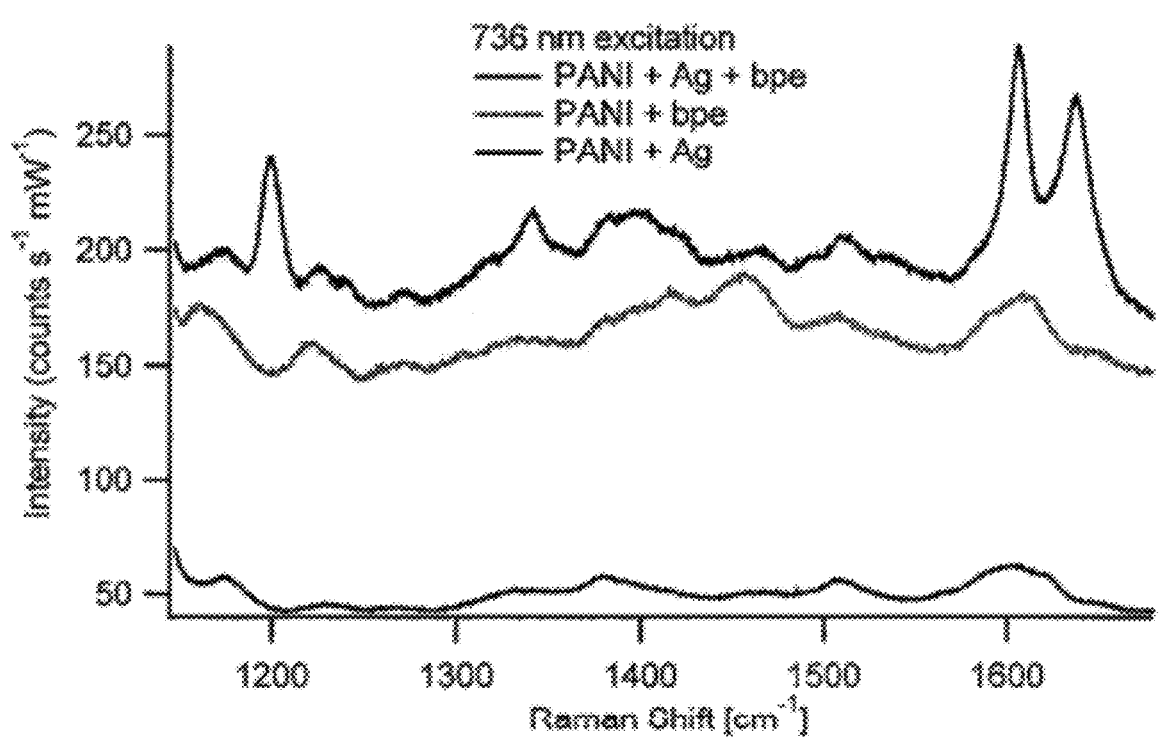
FIG. 9 shows a plot of Raman shift versus intensity for a SERS analysis of (a) a porous asymmetric PANI membrane with a deposited layer of silver; (b) a porous asymmetric PANI membrane with bipyridylethylene (bpe); and (c) a porous asymmetric PANI membrane with a deposited layer of silver and bpe.

The SERS signal arising from the analyte 1,2-bis(4-pyridyl)ethylene)bpe) is much stronger when deposited on the metal-PANI composite, where the metal was silver, than with comparison trials of PANI membrane with bpe and no metal or a PANI membrane with silver and no bpe. There is barely any SERS signal arising from the latter two samples (see FIG. 9). The metal-PANI composite of the present invention clearly enhanced the analytical results.

The SERS signal is much stronger with the metal-PANI composite, where the metal was silver, with 1,2-bis(4-pyridyl)ethylene (bpe) deposited on the silver than with the comparison trials of PANI membrane with bpe or a PANI membrane with silver alone from which there is barely any SERS signal. See FIG. 9 The combination of bpe with the metal-PANI composite of the present invention clearly enhances the analytical results.

Through the process of the present invention, the formation of metals on reductive PANI surfaces can be controlled by tailoring the surface chemistry and redox potential. A wide range of metal, e.g., silver, morphologies can be achieved by selection of dopant, the resultant metal morphologies ranging from fibers to sheets to cubes to hemispheric yarn-like balls. The sizes of the deposited metal structures could also be varied from a few nanometers to several microns. Only small difference in reduction potential between platinum ions ($Pt^{2+}$) and PANI lead to growth of a monodispersed platinum nanoparticles (5 nm in size) spread evenly on top the PANI membrane surface. The stretching of PANI dense films also was shown to influence to deposition of metal, e.g., silver, on the film surface. Facile synthesis of nanostructured metals and nanoparticle combinations on reductive substrate surfaces provide great potential for highly effective catalytic surfaces or for use in low cost devices associated with high sensitivity detection using SERS.

The composite materials of the present invention may further have application in surface processing, catalysis (e.g., in fuel cells or other chemical reactions), as modified surface electrodes, for anticorrosion and for biosensors.

The present invention is more particularly described in the following examples which are intended as illustrative only, since numerous modifications and variations will be apparent to those skilled in the art.

Polyaniline emeraldine base (EB) powder was obtained from Neste Oy. N-methyl-2-pyrrolidone (99%, Aldrich) was dried using a 4 Angstrom) molecular sieve. Heptamethylenimine (98% Acros), $AgNO_3$ (99+% Aldrich), $AuCl_3$ (99.9% Aldrich) and $K_2PtCl_4$ (99.9% Aldrich) were used as received without further purification.

Example A

Fabrication of PANI porous asymmetric membranes was achieved employing a phase inversion method using water as a coagulation bath. Following a typical procedure, 3.70 grams (g) of N-methyl-2-pyrrolidone (NMP) was placed into a 12.0 milliliter (mL) Teflon vial. Then, 0.31 g of heptamethylenimine (HPMI) was added to the vial. The vial was sealed with a Teflon cap and maintained in an oven at 60° C. for 5 minutes. Then, 1.00 g of EB powder was added to the vial. The solution was slowly stirred with a homogenizer and slowly ramped up to 5000 rpm for 25 minutes. The EB/HPMI molar ratio was 1:1 (the moles of EB were calculated based on the tetrameric repeat unit). The resulting EB solution was poured onto a glass plate and spread into a wet film using a gardener's blade (Pompano Beach, Fla.) with a preset thickness. The wet film was then immersed into the water bath and held in the water bath for more than 24 hours. The resulting membrane was then dried under vacuum at room temperature for 12 hours before any subsequent processing. The membranes were immersed in a 0.1 M aqueous acid solution for about 24 hours.

Example 1

Metallization

The porous asymmetric PANI membranes from example A were then immersed into selected metal-ion solutions for a time period ranging from several seconds to about 24 hours depending upon the rate of reaction. 100 millimole (mM) metal-ion solutions were prepared using as-purchased $AgNO_3$, $AuCl_3$ and $K_2PtCl_4$ without further purification.

The structure of the doped PANI membranes and metal PANI membrane composites were studied by X-ray diffraction (XRD) with a Siemans D5000 four-circle diffractometer with a Cu K$\alpha$ radiation source ($\lambda$=0.15418). Normal 0-20 scans were performed on the membrane and composite samples to determine their crystallographic orientation. SEM micrographs of the metal-PANI composites were taken using a JEOL 6300FXV SEM and FEI Quanta FEG ESEM.

Example 2

SERS

Nanostructured silver was grown on a citric acid-doped porous PANI asymmetric membrane and exhibited a sheet-like morphology having sharp edges (see FIG. 5). That composite structure was tested as a suitable SERS substrate. The results of the SERS screening for 1,2-bis(4-pyridyl)ethylene, (bpe), deposited on the silver achieved the results shown in FIG. 9. It can be seen that the SERS signal was much stronger with the metal-PANI composite, where the metal was silver, with 1,2-bis(4-pyridyl)ethylene (bpe) deposited on the silver than with the comparison trials of PANI membrane with bpe (and no metal) or a PANI membrane with silver alone from which there was barely any SERS signal. See FIG. 9. The metal-PANI composite of the present invention clearly enhanced the analytical results.

Example 3

Catalysis

Figure 8:
FIGS. 8(a-c) show SEM micrographs of palladium particles deposited on porous asymmetric PANI membranes at different magnifications.

Nanostructured palladium was grown on a porous PANI asymmetric membrane by immersion of the membrane in a solution of palladium nitrate in nitric acid. It exhibited a typical morphology seen in FIG. 8. That composite structure was tested for its catalytic activity in the hydrogenation of diphenylacetylene. The starting material of diphenylacetylene was placed in a reaction vessel using toluene or methanol as the solvent and the catalyst loading was controlled at about 1 mole percent (compared to the amount of diphenylacetylene). Hydrogen gas (about 1 atm) was then charged into the reaction vessel using a hydrogen balloon over a sixteen-hour period. Analysis of the resultant product by IR and $^1$H-NMR indicated that the diphenylacetylene had been converted to the wholly hydrogenated product of bibenzyl. It is worth noting that the catalytic efficiency is higher than the commercially available palladium nano-catalyst Pd-EnCat™ (Aldrich), which produces the complete hydrogenation product in 18 hours with a catalyst loading of 5 mole percent (see, for comparison, Bremeyer et al, Synlett 2002, 11, 1843).

Further testing showed that the catalyst could be easily recovered and repeatedly used for at least seven times without significant loss of catalytic activity. Further testing on the minimum amount of catalyst on a mole percent basis suggests that catalyst loadings of Pd on PANI could go as low as 0.1 mole percent while still retaining its catalytic activity. Although relatively slow compared to the commercially available Pd on C hydrogenation catalyst, an advantage of the membrane based catalytic system is the significantly improved catalytic selectivity. Under such a low catalyst loading, cis-stilbene could be clearly identified and its ratio could be controlled by simply varying the reaction time. For example, a 72 percent selectivity of cis-stilbene was obtained with the total conversion of diphenylacetylene after 16 hours under such conditions. The complete hydrogenation of diphenylacetylene to afford the bibenzyl was achieved within 48 hours.

Example 4

Catalysis

The same nanostructured palladium-PANI composite catalyst as in example 3 was used in this example. This composite palladium-PANI structure was tested for its catalytic activity in the hydrogenation of trimethyl-(4-aminophenylethynyl)-silane. The starting material of trimethyl-(4-aminophenylethynyl)-silane was placed in a reaction vessel with toluene or methanol as the solvent and the catalyst loading based on the amount of Pd was controlled at about 1 mole percent. Hydrogen gas (about 1 atm) was then charged into the reaction vessel using a hydrogen balloon over a sixteen-hour period. Analysis of the resultant product by IR and $^1$H-NMR indicated that the starting alkyne had been converted to the wholly hydrogenated product of para-aminophenyl-trimethylsilane-ethane without any signs of the alkene intermediate

Example 5

Catalysis

The same nanostructured palladium-PANI composite catalyst as in example 3 was used in this example. This composite palladium-PANI structure was tested for its catalytic activity in the hydrogenation of 1-phenyl-3-ethoxycarbonyl-propyne. The starting material of 1-phenyl-3-ethoxycarbonyl-propyne was placed in a reaction vessel with toluene or methanol as the solvent and and the catalyst loading based on the amount of Pd was controlled at about 5 mole percent. Hydrogen gas (about 1 atm) was charged into the reaction vessel over an initial four-hour period. Analysis of the resultant product after four hours by IR and $^1$H-NMR indicted that the 1-phenyl-3-ethoxycarbonyl-propyne had been converted (70% conversion to product) to a mixture of 65 percent of the alkene (ethyl cis-cinnamate) and 35 percent of the alkane (ethyl hydrocinnamate). Reaction was continued for a total of sixteen hours at which point analysis indicated that the 1-phenyl-3-ethoxycarbonyl-propyne had been converted (96% conversion to product) to a mixture of 26 percent of the alkene and 74 percent of the alkane. Note that the partially hydrogenated product, i.e., the ethyl-cis-cinnamate was observed in the final product. From the NMR it seemed likely that the hydrogenation could be controlled kinetically for selectivity.

Although the present invention has been described with reference to specific details, it is not intended that such details should be regarded as limitations upon the scope of the invention, except as and to the extent that they are included in the accompanying claims.

What is claimed is:

1. An electrodeless method of forming a metal-PANI composite comprising: contacting a metal ion solution with a PANI porous asymmetric membrane comprising at least one surface and an underlying layer, wherein the PANI porous asymmetric membrane is doped with an acidic dopant selected from the group consisting of hydrochloric acid, phosphoric acid, citric acid, mandelic acid, trifluoroacetic acid, para-toluenesulfonic acid, and combinations thereof and wherein said metal ion is characterized as its salt form having a reduction potential greater than that of the polyaniline, for a period of time sufficient to deposit the metal onto at least one surface of the membrane such that (i) said underlying layer is substantially free from the deposited metal and (ii) said metal deposited onto the at least one surface of the membrane is characterized as having a morphology that corresponds to said acidic dopant.

2. The method of claim 1 wherein the metal is selected from the group consisting of silver, gold, platinum, palladium, and combinations thereof.

3. The method of claim 1 wherein the metal is silver.

4. An electrodeless method of catalyzing a hydrogenation reaction to obtain a hydrogenated product comprising:

preparing a metal-PANI composite by contacting a metal ion solution with a PANI porous asymmetric membrane having at least one surface and an underlying layer, wherein the PANI porous asymmetric membrane is doped with an acidic dopant selected from the group consisting of hydrochloric acid, phosphoric acid, citric acid, mandelic acid, trifluoroacetic acid, para-toluenesulfonic acid, and combinations thereof and wherein said metal ion is characterized as its salt form having a reduction potential greater than that of the polyaniline, for a period of time sufficient to deposit the metal at least one surface of the membrane such that (i) said underlying layer is substantially free from the deposited metal and (ii) said metal deposited onto the at least one surface of the membrane is characterized as having a morphology that corresponds to said acidic dopant, the metal being selected from the group consisting of platinum, palladium, and mixtures thereof, reacting an unsaturated organic compound with hydrogen for sufficient time in the presence of the metal-PANI composite to produce a hydrogenated product, and and, recovering the hydrogenated product.

5. The method of claim 4 wherein the metal is palladium.

6. The method of claim 4 wherein the metal has nanoscale structural dimensions.

7. A method of carrying out surface-enhanced Raman spectral analysis of an analyte comprising:

providing a metal-PANI composite of claim 1, wherein the metal is either silver or gold;

bringing an analyte into effective contact with said metal-PANI composite;

illuminating the metal-PANI composite with radiation of at least one wavelength for causing elemental-state particles to produce a plasmon field and for causing said plasmon field to interact with molecules of said analyte, in such a manner, so as to produce Raman photons; and, collecting scatted radiation emitted from said metal-PANI composite for spectral analysis.

8. The method of claim 7 wherein said PANI is doped with an acidic dopant from the group of hydrochloric acid, phosphoric acid, citric acid, madelic acid, trifluoroacetic acid, para-toluenesulfonic acid, and combinations thereof.

9. The method of claim 8 wherein the acidic dopant is citric acid.

10. The method of claim 7 wherein said metal has nanoscale structural dimensions.

* * * * *